United States Patent [19]

Libertucci

[11] Patent Number: 4,911,156
[45] Date of Patent: Mar. 27, 1990

[54] ELASTIC LEG WRAP FOR HORSES

[76] Inventor: Michael J. Libertucci, R.D. 6, Smith Rd., Amsterdam, N.Y. 12010

[21] Appl. No.: 301,359

[22] Filed: Jan. 25, 1989

[51] Int. Cl.$^4$ .............................................. A61F 13/00
[52] U.S. Cl. ..................................... 128/165; 128/155; 128/157; 128/169; 128/170
[58] Field of Search ............ 128/157, 165, 166, 166.5, 128/171, 169, 170, 155

[56] References Cited

U.S. PATENT DOCUMENTS

| | | |
|---|---|---|
| 783,280 | 2/1905 | Jagers .................................... 128/169 |
| 1,161,286 | 11/1915 | Bowman ............................. 128/170 |
| 2,449,410 | 9/1948 | Polinsky . |
| 2,647,510 | 8/1953 | Topmiller . |
| 2,756,746 | 7/1956 | Munrett . |
| 3,115,879 | 12/1963 | Kaplan ................................ 128/165 |
| 3,209,516 | 10/1965 | Hyman . |
| 3,209,517 | 10/1965 | Hyman . |
| 3,338,028 | 8/1967 | Freeman . |
| 3,390,680 | 7/1968 | Marcum ............................. 128/169 |
| 3,504,672 | 4/1970 | Moon . |
| 3,724,457 | 4/1973 | Klatte .................................... 128/157 |
| 3,880,161 | 4/1975 | Fossel . |
| 4,140,116 | 2/1979 | Hampicke . |
| 4,370,978 | 2/1983 | Palumbo . |
| 4,424,809 | 1/1984 | Yovankin . |
| 4,470,411 | 9/1984 | Hoyt, Jr. . |
| 4,532,921 | 8/1985 | Von Torklus et al. . |
| 4,632,105 | 12/1986 | Barlow . |
| 4,685,278 | 8/1987 | Mitsuoka . |
| 4,787,381 | 11/1988 | Hubbard et al. .................... 128/156 |

FOREIGN PATENT DOCUMENTS 425802 6/1911 France ............................... 128/165

Primary Examiner—Richard J. Apley
Assistant Examiner—N. Paul
Attorney, Agent, or Firm—Schmeiser, Morelle & Watts

[57] ABSTRACT

An improved horse leg wrap wherein a plurality of elastic strips are secured together and held in a spaced apart relationship from one and other by nylon webbing. Silicone friction beads lay parallel to the elastic strips and run the length of the leg wrap, adjacent silicone beads being at least one quarter inch away from any adjacent bead portion.

15 Claims, 2 Drawing Sheets

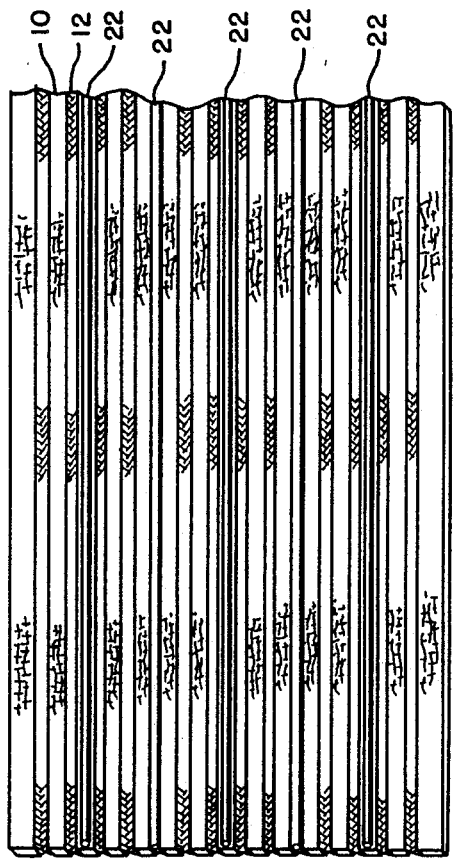
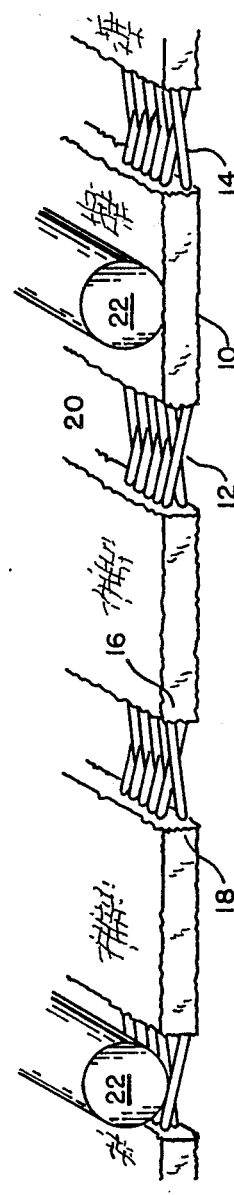

ELASTIC LEG WRAP FOR HORSES

FIELD OF THE INVENTION

Generally this invention relates to horse leg supports. More specifically this invention is an improved elastic leg wrap for horses.

BACKGROUND OF THE INVENTION

It has been common practice to wrap the lower portion of a horse's legs during training and racing. The type of wrap which is generally used is similar to commonly found elastic bandages which are made of a knitted material and have a significant cotton content. However, as may be expected, the dimensions for a leg wrap for horses is generally significantly larger then that for humans, the horse leg wrap generally measuring 4½ inches in width and 9 feet in length. The horse leg wrap serves a dual purpose, namely, cushioning and support. The bandage acts as a cushioning guard to prevent abrasions and minor contusions which result from common impacts which the horses encounter. The support aspect of the bandage serves to reinforce the leg thereby reducing the possibility of fractures and the like.

Although, these bandages have found wide acceptance and numerous variations have been proposed, two main problems still exist with the bandages presently available.

One of the primary difficulties encountered with this type of bandage may be broadly defined as application. First, in order to be effective the bandage must be stretched as it is applied so that it is tight enough to support the horse's leg but not so tight that circulation is limited. Secondly, it is also important that the bandage, which is applied in a spiral configuration, does not overlap to too great a degree as this would restrict movement of the horses leg. Added to this already sensitive task is the fact that the bandage must be secured sufficiently to remain in place while the horse is running. This latter problem has been difficult to overcome since the constant impact present while the horse is running imparts a substantial downward motion to the bandage. To prevent the bandage from slipping while the horse is running the frictional forces created between both the bandage and the horses leg and the bandage and other portions of the same bandage must be greater than the downward motion which is induced during impact. Recognizing this difficulty, a number of inventions have directed their efforts to protective boots or coverings for a horses leg which are simply strapped around the lower portion of the horses leg and do not attempt to provide the type of support found with the elongate elastic bandages previously used. Thus, while these leg guards serve a specific purpose they do not provide the type of support which is obtained with a wrap around bandage.

Another problem commonly encountered is the increased weight of the bandage when the horse trains or races on a wet track. However, since the safety of the horse is more important than the added weight this shortcoming has been accepted as being unavoidable. As previously mentioned the dimensions of the bandage for horses are relatively consistent and are generally necessary in order to provide the above enumerated benefits. Therefore, reducing the size of the bandage in order to reduce weight is not a viable alternative. Thus, it is commonly accepted in the industry that when a horse is training in wet conditions the leg bandages will simply become saturated. However, since it is important for the horse to wear the protective bandage the difficulties caused by a saturated bandage were generally not considered. In fact, studies which we have done on various bandages indicate that in wet conditions a bandage may increase in weight anywhere from 12 to 32 ounces which of course if multiplied by the number of bandages would result in a 48 to 128 ounce overall increase in the weight being carried by the horse. This problem is further exacerbated by the fact that the weight is located at the worst possible point, namely the lower portion of the horses leg, and thus significantly hampers the horses performance and may lead to muscle strain.

SUMMARY OF THE INVENTION

The subject invention is an elastic bandage having a plurality of elastic strips separated by nonabsorbent nylon webbing. The nonabsorbent nylon segments reduce the overall absorbency of the leg wrap thereby reducing the weight of the saturated leg wrap by at least 33% over any similar sized wrap.

Furthermore, five silicone beads are placed along the length of the wrap and are substantially parallel to the elastic strips and the nylon segments. These silicone beads are spaced apart from each other by at least one elastic strip and one segment of nylon webbing. Adjacent beads are sufficiently set apart from each other so that upon application there is no significant bead overlap which would tend to limit circulation in the horse's leg. In addition, the nylon webbing forms somewhat of a trough between crestlike elastic strips and therefore upon wrapping of the bandage the silicone beads tend to settle into these troughs so that the bandage is secured in place not only by the increased friction of the silicone but also by the mating of the beads with the troughs.

Thus, the subject invention provides an improved horse leg wrap which is significantly lighter than present leg wraps when saturated and resists sliding during use.

BRIEF DESCRIPTION OF THE DRAWINGS

FIG. 2 is a top plan view of a section of the wrap showing the bead configuration;

FIG. 3 is a perspective view in elevation and also exploded showing the silicone beads and the webbing configuration of the nylon.

DETAILED DESCRIPTION OF THE DRAWINGS

Figure 1:
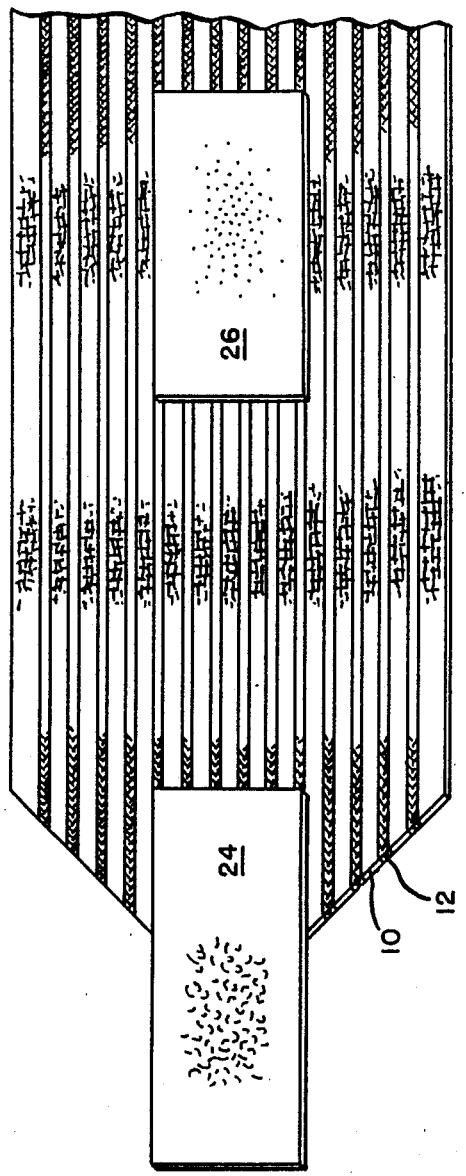
FIG. 1 is a top plan view of the invention showing means for securing the invention to the horse.

As shown in FIG. 2 the invention consists of elastic strips 10 which run parallel to each other and are separated by nylon webbing 12. The elastic strips are only elastic in their lengthwise direction. The elastic portions of the wrap consist of 28% cotton, 64% nylon and 8% spandex. As in all other prior art it is necessary to include cotton or some similar substance in the elastic material in order to soften the elastic so that it will not irritate the horses leg. The cotton also provides a certain degree of friction to reduce the slippage one would encounter if the wrap were made of simply nylon or spandex.

As shown in FIG. 3 the nylon webbing 12 consists of a plurality of nylon fibers 14 which are interwoven across the width of the wrap. The fibers are woven so as to exit the top 16 of one elastic strip and enter toward the bottom 18 of the adjacent elastic strip and then proceeding on to the top of the next adjacent strip and so on until the weave is completed. Adjacent nylon fibers alternate from top to bottom thereby forming a criss cross configuration as shown at 20.

As shown in FIGS. 1 and 2 and in the exploded FIG. 3, silicone beads 22 are applied to the surface of the material sometimes being applied along an elastic strip and at other times along a nylon web. I have found it necessary to separate the silicone beads 22 so that adjacent beads are at least a quarter inch apart from each other and preferably a half an inch apart from each other, when they are separated by at least two elastic strips and two segments of nylon webbing. In this way, when the wrap is applied to the horse's leg in a spiral fashion the silicone beads will not overlap to such a degree that circulation is significantly limited.

Figure 4:
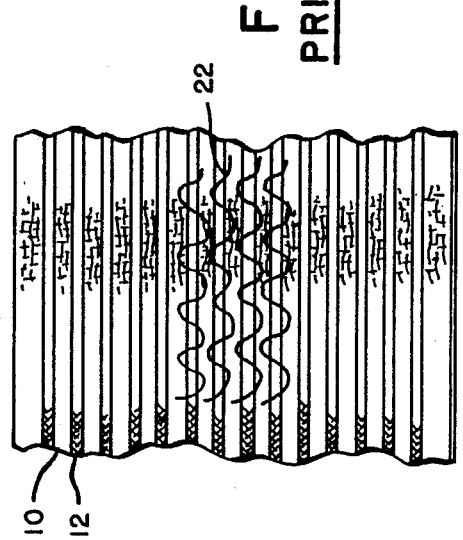
FIG. 4 is a top plan view of material previously available prior to the development of the subject invention.

It will be noted as shown in FIG. 4 the previously available configuration for this material included a plurality of silicone beads in matching sine waves with four of these beads placed toward the center of the material in a configuration having an entire width less than one inch. This material was used in small segments for several purposes such as at the top of no slip stockings and for knee brace securements (as shown in the enclosed advertising).

With the sine wave configuration shown in the prior art sufficient friction was obtained to hold up stockings, however, with the knee brace, straps above and below the knee and an improved slotted pivot substantially avoided slippage and only the bottom strap utilized the silicone beads. It should be noted also that the purpose for the nylon webbing as shown in the FIG. 4 embodiment of the prior art was to allow for breathing since this material was not applied in an overlay or spiral fashion but simply encircled the subject a single time. Thus, the webbing allowed for communication with the otherwise covered surface. Therefore, the use of webbing in a longer bandage was contraindicated. It should be noted, that the use of the nylon webbing has no significant effect on weight when the item is dry. Nevertheless, working in the horse industry I recognized that the nylon webbing could provide a different benefit, namely, reduced overall absorbtion. However, I discovered that when I had the manufacturer produce long strips, of approximately nine feet, as required for horse leg wrappings, the configuration of the silicone beads resulted in an overlap that reduced circulation which was of course unacceptable. Modifications to the silicone beads resulted in the subject invention as shown in FIG. 2.

When the silicone beads were moved in order to avoid interference with circulation, I also discovered that the now straight beads, being parallel to the webbing would tend to reside in these trough like webs and thereby further reduce slippage.

FIG. 1 discloses attachment means 24 and 26 which are commonly marketed under the trademark Velcro. In this configuration the material portion 24 is a strip approximately five inches long secured to one end of the leg wrap and extending outwardly therefrom, and a hook portion 26, approximately four and one half inches long, which is secured on the outside or bottom 18 of the bandage four and one half inches back from portion 24, so that during the last wrap said hook and material portions will interact to secure the wrap in place.

As shown in FIGS. 1-3 the elastic strips are preferably 3/16ths of an inch wide and the nylon webbing is preferably 3/32nds of an inch wide. With the width of the outermost elastic strips being 5/16ths of an inch wide and the entire wrap being 4½ inches wide and 9 feet long.

In addition to the preferred embodiment described above, the size of the wrap can vary between 3½ and 6 inches in width and between 6 and 12 feet in length. All size variations described above would provide sufficient support and exhibit the same benefits over standard knitted elastic synthetics.

In operation, the bandage is rolled around the horse's leg with the silicone beads 22 facing inward against the leg. The wrap is applied in a consistent spiral fashion to avoid numerous overlaps of the silicone beads. It should be noted, that depending on the angle of the spiral one or more silicone beads may overlap. However, since the beads are substantially straight in their configuration they will only overlap at a relatively small number of places and therefore have no significant effect on the circulation of the horse's leg. In the last wrap the hook portion 26 faces outward and the material strap portion 24 secures thereto. Even if specific attention is not paid to the nestling of the silicone beads within the troughs formed by the nylon webbing 12 said nestling will take effect. However, the person applying the wrap may choose to pay greater attention to the bead locations and thereby nestle the beads within the troughs with more consistency. This nestling also acts as a guide to the person applying the bandage resulting in a smoother more consistent spiral.

It should be appreciated that while the above describes the preferred embodiment of this invention it is anticipated that those familiar with the art may make variations without departing from the spirit of the invention which is intended to be limited only by the appended claims.

I claim:
1. An elastic leg wrap for horses comprising:
   a plurality of separate parallel elastic strips;
   webbing securing each elastic strip to its adjacent strip, said webbing and elastic strips forming a wrap at least 60 inches in length and 3½ inches in width; a plurality of friction beads secured to said wrap and lying substantially parallel to said elastic strips; and
   means for fastening one end of the wrap to another portion of said wrap.
2. The invention of claim 1 wherein said webbing is substantially nonabsorptive.
3. The invention of claim 1 wherein said friction beads are substantially straight.
4. The invention of claim 3 wherein said friction beads are made of silicone.
5. The invention of claim 3 wherein there are at least one elastic strip and one segment of webbing between each adjacent friction bead.
6. An elastic leg wrap for horses comprising;
   an elastic wrap having a plurality of nonabsorptive segments;
   a plurality of substantially straight friction beads lengthwise along said wrap; and
   means for securing one end of said leg wrap to another portion of said elastic leg wrap whereby said friction beads serve to reduce slippage of said elastic leg wrap.

7. The invention of claim 6 wherein said elastic leg wrap further comprises:
a plurality of parallel elastic strips; and
nonabsorptive webbing securing each elastic strip to its adjacent strip.

8. The invention of claim 7 wherein said webbing further comprises a plurality of strands forming a cross hatch, each of said strands exiting an elastic strip toward the top surface of said strip and entering the adjacent strip toward the bottom surface, adjacent strands alternating whereby one strand exits toward the top surface of elastic strip and the adjacent strip exits toward the bottom surface of said strip thereby forming a criss cross pattern.

9. The invention of claim 8 wherein the beads are made of silicone.

10. The invention of claim 9 wherein the web strands are nylon.

11. The invention of claim 7 wherein said elastic strips are elastic only in the lengthwise direction.

12. An elastic leg wrap for horses comprising:
an elongate elastic wrap having a plurality of nonabsorptive segments;
a plurality of friction beads along the length of said wrap, each of said beads being at least one fourth inch away from any adjacent bead along its entire length whereby said friction beads serve to reduce slippage of said elastic leg wrap.

13. The invention of claim 12 wherein said friction beads are at least one half inch away from any adjacent bead along their entire lengths.

14. The invention of claim 12 wherein said friction beads are substantially straight and lie parallel to the nonabsorptive segments.

15. The invention of claim 12 wherein said wrap further comprises a plurality of elastic strips, said elastic strips being secured to each other by parallel portions of nonabsorptive webbing, at least one elastic strip and two nonabsorptive webs lying between each friction bead.

* * * * *